US006815579B1

(12) United States Patent
Kunst et al.

(10) Patent No.: US 6,815,579 B1
(45) Date of Patent: Nov. 9, 2004

(54) PLANT LONG CHAIN FATTY ACID BIOSYNTHETIC ENZYME

(75) Inventors: Ljerka Kunst, North Vancouver (CA); Sabine Clemens, Vancouver (CA)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 09/787,962

(22) PCT Filed: Jul. 21, 2000

(86) PCT No.: PCT/CA00/00860

§ 371 (c)(1), (2), (4) Date: Mar. 22, 2001

(87) PCT Pub. No.: WO01/07586

PCT Pub. Date: Feb. 1, 2001

Related U.S. Application Data

(60) Provisional application No. 60/145,013, filed on Jul. 22, 1999.

(51) Int. Cl.[7] .......................... A01H 5/00; C12N 15/82

(52) U.S. Cl. ...................... 800/281; 800/298; 800/306; 800/322; 435/419; 435/440; 536/23.6

(58) Field of Search ................................ 800/281, 298, 800/306, 322; 435/419, 440, 69.1, 468, 320.1; 536/23.6, 23.2

(56) References Cited

U.S. PATENT DOCUMENTS

| | | | |
|---|---|---|---|
| 4,684,611 | A | 8/1987 | Schilperoort et al. |
| 4,743,548 | A | 5/1988 | Crossway et al. |
| 4,801,540 | A | 1/1989 | Hiatt et al. |
| 4,940,838 | A | 7/1990 | Schilperoort et al. |
| 4,945,050 | A | 7/1990 | Sanford et al. |
| 5,015,580 | A | 5/1991 | Christou et al. |
| 5,149,655 | A | 9/1992 | McCabe et al. |
| 5,231,019 | A | 7/1993 | Paszkowski et al. |
| 5,464,763 | A | 11/1995 | Schilperoort et al. |
| 5,466,587 | A | 11/1995 | Fitzpatrick-McElligott et al. |
| 5,597,946 | A | 1/1997 | Jaynes et al. |
| 5,723,756 | A | 3/1998 | Peferoen et al. |

FOREIGN PATENT DOCUMENTS

| | | |
|---|---|---|
| WO | WO 9515387 | 6/1995 |
| WO | WO 9613582 | 5/1996 |
| WO | WO98/54954 | 12/1998 |

OTHER PUBLICATIONS

Huang et al, Genetics 141(4):1275, 1995, abstract.*

Bork et al, TIG 12(10): 425–427, Oct., 1996.*

Brenner, S., TIG 15(4): Apr. 1999.*

Smith et al, Nature Biotechnology 15: 1222–1223, Nov. 1997.*

Doerks et al, TIG 14(6): Jun. 1998.*

Broun et al, Science 282: 1315–1317, Nov. 13, 1998.*

Van de Loo et al, PNAS, USA 92: 6743–6747, Jul. 1995.*

De Luca, V. AgBiotech News and Information 5(6): 225N–229N, 1993.*

Todd et al., "KCS1 encodes a fatty acid elongase 3–ketoacyl–CoA synthase affecting wax biosynthesis in *Arabidopsis thanliana,*" *Plant J.* 17(2):119–130, Jan. 1999.

Bevan et al., GenBank Accession No. AL023094, Apr. 29, 1998.

Clough et al., "Floral dip: a simplified method for Agrobacterium–mediated transformation of *Arabidopsis thaliana,*" *The Plant Journal* 16(6):735–743, 1998.

Haque et al., "Inheritance of Leaf Epicuticular Wax Content in Rice," *Crop Sci.* 32:865–868, 1992.

James et al., "Isolation of EMS–induced mutants in Arabidopsis altered in seed fatty acid composition," *Theor Appl Genet* 80:241–245, 1990.

Jefferson et al., "GUS fusions: β–glucuronidase as a sensitive and versatile gene fusion marker in higher plants," *The EMBO Journal* 6(13):3901–3907, 1987.

Koncz et al., "The promoter of $T_L$ –DNA gene 5 controls the tissue–specific expression of chimaeric genes carried by a novel type of Agrobacterium binary vector," *Mol. Gen. Gent.* 204:383–396, 1986.

Kunst et al., "Fatty acid elongation in developing seeds of *Arabidopsis thaliana,*" *Plant Physiol. Biochem.*, 30(4): 425–434, 1992.

Lassner et al., "A Jojoba β–Ketoacyl–CoA Synthase cDNA Complements the Canola Fatty Acid Elongation Mutation in Transgenic Plants," *The Plant Cell.*, 8:281–292, Feb. 1996.

Lemieux et al., "Mutants of Arabidopsis with alterations in seed lipid fatty acid composition," *Theor Appl. Genet.* 80:234–240, 1990.

Millar et al., "Very–long–chain fatty acid biosynthesis is controlled through the expression and specificity of the condensing enzyme," *The Plant Journal* 12(1):121–131, 1997.

(List continued on next page.)

*Primary Examiner*—Elizabeth F. McElwain
(74) *Attorney, Agent, or Firm*—Klarquist Sparkman LLP

(57) ABSTRACT

In various aspects, the present invention provides nucleic acid sequence encoding all or part of a new plant long chain fatty acid condensing enzyme (a fatty acid elongase), designated herein as KCS2 (for beta-ketoacyl-coenzyme A synthase 2). In some embodiments, KCS2 may mediate the biosynthesis of C18, C20, C22 and C24 fatty acids. The activity of the enzyme is typically characterized by two carbon (malonyl-CoA) additions to C16, C18, C20 and C22 moieties (C16–C22 acyl CoA molecules), i.e. condensation of malonyl-CoA with a C16, C18, C20 or C22 acyl-CoA. The fatty acids produced by the enzyme may for example be saturated 18:0, 20:0, 22:0 and 24:0 fatty acids. The invention includes recombinant nucleic acid molecules comprising a heterologous nucleic acid coding sequence encoding the plant long chain fatty acid condensing enzyme.

38 Claims, 1 Drawing Sheet

OTHER PUBLICATIONS

Millar et al., "CUT1, an Arabidopsis Gene Required for Cuticular Wax Biosynthesis and Pollen Fertility, Encodes a Very–Long–Chain Fatty Acid Condensing Enzyme," *The Plant Cell*, 11:825–838, May 1999.

O'Toole et al., "Genotypic Variation in Epicuticular Wax of Rice," *Crop. Science* 23:392–394, Mar.–Apr. 1983.

Post–Beittenmiller, "Biochemistry and Molecular Biology of Wax Production in Plants," *Annu. Rev. Plant Physiol. Plant Mol. Biol.* 47:405–430, 1996.

Todd et al., "KCS1 encodes a fatty acid elongase 3–ketoacyl–CoA synthase affecting wax biosynthesis in *Arabidopsis thaliana,*" *The Plant Journal* 17(2):119–130, 1999.

* cited by examiner

Figure 1

```
1     tgttgtggag gacttgtgag aaccaccacc agagtccgac atcgcgatca
51    cggagtagag aaagtcaaaa ctacttctct cagacggatt agtttggttt
           kcs3->
101   gctggagatt gttccaagaa agagaaacgt taggagcaaa caaacaaaag
151   agaaaagacg atgatgactg atgagagctt taacaaaaaa ataaaatgag
201   agagctcaac gggtagaatt gtgagacttg agagagtgtt tcctatttaa
251   ggcatgcgat tagtgtttat tacgagaatg ccaccgaacg agtacatatt
301   aatgtatagt atgttaatga tagtctaact aaaatttggt ttttattgaa
351   atagaatttt gtaagaataa tgaggatctg taatatagct ggatttgcat
401   taaatcgtac gccgttggta atcgaaatta gttaaataaa tgttttagca
451   tataatgttg gtgcttccga catgtttatt ggacaataat accatatttt
501   ttctttggga tcttaaaaaa attgaggaag aaaatagtaa aatagtcaaa
551   cttaggttac atcataatgg gccaattctt tgagttgtga ttgatctcca
601   aagatataca tagatttaca caagatcaaa agaaaaacaa ttgggcctaa
651   accccaagcc catatcaacg tccattatca ttaagattcc tttttttctt
701   gaaatttgaa aatttgaaat tcgattcaaa tctactctct ctgttttttt
751   cccataaaaa tctgaaaaac cagaagcttc ttcatcactt ttcctcttga
801   tatcttccat tagttggccg atacacatga cgccaaatac atcaatggcg
851   actcttctct gtttttttagt tatatcaaac tcccacccaa cctgcagaag
901   aaaaaatggt gtctataaac acatcccctt acgatttctt ctctatctct
951   ctcacagtat ctatatatac gcacacaaac ccagattcag tttctcatca
1001  gtatcatcaa caaaaatatc aaagattctg ctttagaaac tgtccATGga
                    kcs1 ->           <- kcs4
1051  tgctaatgga ggacctgtac agatccggac ccaaaactac gtcaagcttg
1101  gttatcacta tctgatcact cacttttta aactcatgtt cctccctcta
1151  atggctgttt tgttcatgaa tgtctcattg ttaagcctaa accatcttca
1201  gctctattac aattccaccg gattcatctt cgtcattact ctcgccattg
1251  tcggatccat tgtcttcttc atgtctcgac ctagatccat ctaccttcta
1301  gattactctt gctacctccc gccttcgagt caaaaagtta gctaccagaa
1351  attcatgaac aactctagtt tgattcaaga tttcagcgaa acttctcttg
1401  agttccagag gaagatcttg attcgctctg gtctcggtga agagacttat
1451  ttaccggatt ctattcactc tatccctccg cgtcctacta tggctgcagc
1501  gcgtgaagaa gcggagcagg taatcttcgg tgcactcgac aatcttttcg
1551  agaatacaaa aatcaatcct agggagattg gtgttcttgt tgtgaattgt
1601  agtttgttta accctacgcc ttctttatcc gccatgattg ttaacaagta
1651  taagcttaga ggaaacatta agagctttaa ccttggagga atgggatgta
1701  gtgctggtgt tatcgcggta gatctagcta gtgatatgtt acaaatccat
1751  aggaacactt ttgctcttgt ggttagtact gagaacatca ctcagaattg
1801  gtattttggt aacaagaaag caatgttgat ccctaattgc ttgtttagag
1851  ttggtggttc cgcggttctg ctttcgaaca agcctttgga tcgaaaacga
1901  tccaagtata agcttgttca tacggtcagg actcataaag gatctgatga
1951  gaacgcattc aattgtgtgt atcaagaaca agatgagtgt ttgaaaaccg
2001  gagtttcttt gtctaaagat cttatggcta tagctggaga agctttaaag
2051  acgaatatca cttctttggg tcctctggtt cttcctataa gcgagcagat
2101  tctgttcttt gcgacttttg ttgctaagag attgttcaat gacaagaaga
2151  agaagcctta cataccggat ttcaagcttg ctttagatca tttctgtatt
2201  cacgcgggag gtagagccgt gattgatgag ctagagaaga gtttaaagct
2251  ttctccaaaa catgttgagg cgtctagaat gactttgcat agatttggaa
2301  acacttcctc tagctctata tggtatgaat tggcttacac ggaagctaaa
2351  ggaagaatga ggaaaggaaa cagagtttgg cagattgctt ttggtagcgg
2401  gtttaagtgt aacagcgcgg tttgggtggc tcttcgcaat gtcgagccct
2451  cggttaacaa tccttgggaa cattgcatcc atagatatcc ggttaagatc
                                                  <- kcs2
2501  gatctttga
```

PLANT LONG CHAIN FATTY ACID BIOSYNTHETIC ENZYME

CROSS-REFERENCE TO RELATED APPLICATIONS

This is the National Stage of International Application No. PCT/CA00/00860, and filed Jul. 21, 2000, and claims the benefit of U.S. Provisional Application No. 60/145,013, filed Jul. 22, 1999. The provisional application is incorporated herein in its entirety.

FIELD OF THE INVENTION

The invention relates to a condensing enzyme involved in long chain fatty acid production in plants, including related nucleic acid sequences.

BACKGROUND

Living organisms synthesize a vast array of different fatty acids, which are incorporated into complex lipids. These complex lipids represent both major structural membrane components, and are a major storage product in both plants and animals. In plants, very long chain fatty acids (VLCFAs, chain length C20 or longer) are synthesized predominantly in the epidermal cells where they are either directly incorporated into waxes, or serve as precursors for other aliphatic hydrocarbons found in waxes, including alkanes, primary and secondary alcohols, ketones, aldehydes and acyl-esters (for review see Post-Beittenmiller, 1996). VLCFAs also accumulate in the seed oil of some plant species, where they are incorporated into triacylglycerols (TAGs), as in the *Brassicaceae*, or into wax esters, as in Jojoba. These seed VLCFAs include the agronomically important erucic acid (C22:1), that may be used in the production of lubricants, nylon, cosmetics, pharmaceuticals and plasticizers.

VLCFAs are synthesized by a microsomal fatty acid elongation (FAE) system which involves four enzymatic reactions: (1) condensation of malonyl-CoA with a long chain acyl-CoA, (2) reduction to beta-hydroxyacyl-CoA, (3) dehydration to an enoyl-CoA and (4) reduction of the enoyl-CoA, resulting in the acyl-CoA elongated by two carbons. The condensing enzyme catalyzing reaction (1) is a key activity of the FAE system. It is the rate-limiting enzyme of the VLCFA biosynthetic pathway, which controls the amount of VLCFAs produced (Miller and Kunst, 1997). In addition, the condensing enzyme determines the ultimate VLCFA acyl chain length, and thus their uses in seed oil or wax biosynthesis.

Different condensing enzymes acting on, and producing, acyl chains of different length have recently been characterized. Several groups independently identified the first plant fatty acid elongation gene in *Arabidopsis*, FAE1 (James and Dooner, 1990; Kunst et al., 1992; and Lemleux et al., 1990). FAE1 was subsequently cloned and is described in WO9613582 as catalyzing the conversion of C18 fatty acids to C20–C22 fatty acids. The patent WO9613582 suggests that FAE1 will have activity in a very broad host range. In support of this assertion of broad host range activity, it has been shown that FAE1 has the same activity in yeast as in Arabiqopsis (Miller and Kunst, 1997). A Jojoba protein involved in the synthesis of VLCFAs has also been isolated having relatively high homology to FAE1 (52% amino acid identity), and has been shown to have beta-ketoacyl-coenzyme A synthase (KCS) activity (WO9515387). Broad host range activity for genes encoding KCS has been further evidenced by the Jojoba KCS cDNA.

The Jojoba KCS cDNA was able to complement a mutation in a Canola variety of rapeseed (*Brassica napus*), to restore in the variety high levels of VLCFAs (Lassner et al., 1996). An *Arabidopsis* gene (CUT1), required for cuticular wax biosynthesis and pollen fertility, has also been described as encoding a VLCFA condensing enzyme that catalyzes the addition of 2C units to pre-existing C24 or longer fatty acids (Millar et al., 1999).

The broad specificities exhibited by FAE activities provide a means of modifying the synthesis of VLCFAs in a given cell. As evidenced by the accumulation of VLCFAs in tobacco seed expressing FAE1 (Millar and Kunst, 1997), heterologous condensing enzymes may be used to produce VLCFAs in plant species that do not otherwise synthesize VLCFAs. For example, targeted expression of heterologous VLCFA condensing enzymes in seeds may allow the production of crop plants capable of synthesizing VLCFAs of desired lengths in seed oil for industrial applications. New condensing enzymes may also be useful for the manipulation of cuticular waxes which have important functions in many physiological processes in plants, including water balance, protection from UV light, plant-insect interactions, and defense against bacterial and fungal pathogens (Post-Beittenmiller, 1996). As a result, there is a need for new condensing enzymes that may be used alone or in combination with other condensing enzymes to confer on plants and plant tissues the ability to synthesize a range of VLCFAs, including VLCFAs up to C30 in length.

There is also a need for tissue-specific promoters capable of mediating the expression of heterologous condensing enzymes in epidermal cells, which may facilitate the alteration of the wax composition and/or accumulation in plants. This may, in turn, result in the production of crops with increased tolerance to environmental stresses, and/or resistance to pathogens and insects. For example, drought resistance in rice is associated with high wax lines rich in C29, C33 and C35 alkanes (O'Toole and Cruz, 1983; Haque et al., 1992). Increased wax deposition may also be accomplished by overexpression of condensing enzymes with desired acyl chain length specificities using an epidermis-specific promoter, such as the CUT1 promoter (Millar et al., 1999).

The cumulative data, as discussed, from a variety of sources in this field has led to the suggestion that the amounts and acyl chain lengths of VLCFAs, in a wide variety of eukaryotic cells, are regulated by the nature of condensing enzyme expression in the cell (Miller and Kunst, 1997). Condensing enzymes would therefore be useful in a range of biotechnical applications.

SUMMARY

In various aspects, the present invention provides nucleic acid sequence encoding all or part of a new plant long chain fatty acid condensing enzyme (fatty acid elongase), designated herein as KCS2 (for beta-ketoacyl-coenzyme A synthase 2). In some embodiments, KCS2 may mediate the biosynthesis of C18, C20, C22 and C24 fatty acids. The activity of the enzyme is typically characterized by two carbon (malonyl-CoA) additions to C16, C18, C20 and C22 moieties (C16–C22 acyl CoA molecules), i.e. condensation of malonyl-CoA with a C16, C18, C20 or C22 acyl-CoA. The fatty acids produced by the enzyme may for example be saturated 18:0, 20:0, 22:0 and 24:0 fatty acids.

The invention includes recombinant nucleic acid molecules comprising a heterologous nucleic acid coding sequence encoding the plant long chain fatty acid condensing enzyme. In alternative embodiments, the nucleic acid coding sequence may be derived from the *Arabidopsis* KCS2 coding sequence disclosed herein. Alternatively, embodiments include nucleic acids that encode the plant very long chain fatty acid condensing enzyme of the invention, wherein the enzyme has an amino acid sequence that is at least 70% identical to an *Arabidopsis* KCS2 amino acid sequence disclosed herein, when optimally aligned. The nucleic acid coding sequences of the invention also include sequences that hybridize under stringent conditions to a complement of the *Arabidopsis* KCS2 coding sequence disclosed herein. The nucleic acid coding sequences of the invention may also be at least 70% identical to the *Arabidopsis* KCS2 coding sequence, when optimally aligned. Embodiments of the invention include isolated nucleic acid molecules comprising the coding sequences of the invention.

In another aspect, the invention provides recombinant nucleic acid molecules comprising a promoter sequence operably linked to a nucleic acid sequence, wherein the promoter sequence is capable of mediating gene expression in anthers and in very young leaves in *Arabidopsis*. The promoter sequences of the invention may be derived from an *Arabidopsis* KCS2 promoter sequence, as disclosed herein. Promoter sequences of the invention may also hybridize under stringent conditions to the *Arabidopsis* KCS2 promoter sequence disclosed herein. Promoter sequences of the invention may also be at least 70% identical to the *Arabidopsis* KCS2 promoter sequence when optimally aligned.

The invention provides nucleic acid probes comprising probe sequences that hybridize under stringent conditions to a portion of an *Arabidopsis* KCS2 genomic sequence; or are at least 70% identical to the portion of an *Arabidopsis* KCS2 genomic sequence when optimally aligned. The invention also provides methods of isolating a nucleic acid molecule encoding a plant long chain fatty acid condensing enzyme, for example by hybridizing a nucleic acid preparation with the nucleic acid probe of the invention.

The invention provides transgenic cells (such as plant cells), plants and parts thereof, in which the plants or cells comprise the recombinant nucleic acid molecules of the invention. Such plant parts may for example include seeds or oils. Transgenic plants of the invention may have a modified phenotype compared to a non-transgenic plant of the same species, such as a modified lipid content. Methods of producing such transgenic plants are provided, for example by introducing into a plant the isolated nucleic acids of the invention. Progeny plants may be provided, produced by sexual or asexual propagation of the transgenic plants of the invention to produce transgenic descendants of transformed plants.

Purified proteins are provided, encoded by the recombinant nucleic acid molecules of the invention, including plant fatty acid condensing (elongase) enzymes and fragments thereof. Also provided are recombinant vectors comprising the recombinant nucleic acid molecules of the invention.

Antisense nucleic acid molecules are provided, wherein a portion of the nucleic acid coding sequences of the invention are provided in reverse orientation relative to an adjacent promoter sequence. Recombinant antisense nucleic acids of the invention may therefore encode an antisense RNA that hybridizes under stringent conditions to a complement of a portion of the *Arabidopsis* KCS2 coding sequence; or that are at least 70% identical to a portion of the *Arabidopsis* KCS2 coding sequence when optimally aligned. Transgenic plants or plant cells of the invention may include the recombinant antisense nucleic acids of the invention.

In one embodiment, the nucleic acid coding sequences of the invention may be substantially identical to all or part of an *Arabidopsis* KCS2 coding sequence, The nucleic acids of the invention may also include an RNA analog or a nucleic acid complementary to sequences of the invention. In other embodiments, the nucleic acid may be a fragment of one of the above sequences, such as a fragment that is at least 5, 10, 15, 20 or 25 nucleotides in length and that hybridizes under stringent conditions to a genomic KCS2 DNA encoding the nucleic acid sequence. As used herein, the term "genomic sequence" includes either of the strands of a nucleic acid molecule found in the genome of an organism or cell.

In another aspect, the nucleic acids of the invention may include a DNA coding sequence encoding an enzyme of the invention, operably linked to a promoter. Promoters of the invention may be tissue-specific or have specific developmental timing. A promoter of the invention may have a nucleotide sequence substantially identical to all or part of the KCS2 promoter region disclosed herein. Promoters of the invention may be operably linked to alternative DNAs, such as agronomically important nucleic acid sequences.

In one aspect, the invention provides methods for altering the VLCFA, fatty acid or lipid content in a plant or plant tissue, for example by introducing into a plant cell, capable of being transformed and regenerated to a whole plant, a nucleic acid of the invention. Where such nucleic acids are effective for altering the levels of VLCFAs in a plant; a plant containing the nucleic acid of the invention may be recovered having an altered phenotype.

THE DRAWINGS

FIG. 1 shows the coding strand DNA sequence of a KCS2 genomic clone from *Arabidopsis*, containing a 1001 bp long KCS2 promoter region (5' to the initiation codon) and a 1508 bp long KCS2 coding sequence. The initiation (ATG) codon is indicated in all caps (at positions 1046–1048). The FIGURE identifies locations homologous or complementary to oligonucleotide primers (probes) that may be used for amplifying the wild-type *Arabidopsis* KCS2 promoter (shown as kcs3 and kcs4) and the KCS2 coding sequence (kcs1 and kcs2), these sequences are underlined and marked by arrows indicating the putative direction for amplification.

DETAILED DESCRIPTION OF THE INVENTION

The recombinant nucleic acid molecules of the invention may comprise a heterologous nucleic acid coding sequence encoding the plant long chain fatty acid condensing enzyme of the invention. In alternative embodiments, the nucleic acid coding sequence may be derived from the *Arabidopsis* KCS2 coding sequence disclosed herein.

The term "recombinant" means that something has been recombined, so that when made in reference to a nucleic acid molecule the term refers to a molecule that is comprised of nucleic acid sequences that are joined together by means of molecular biological techniques. The term "recombinant" when made in reference to a protein or a polypeptide refers to a protein molecule which is expressed using a recombinant nucleic acid molecule. The term "heterologous" when made in reference to a nucleic acid sequence refers to a nucleotide sequence which is ligated to, or is manipulated to become ligated to, a nucleic acid sequence to which it is not ligated in nature, or to which it is ligated at a different location in nature. The term "heterologous" therefore indicates that the nucleic acid molecule has been manipulated using genetic engineering, i.e. by human intervention.

Sequences may be derived or obtainable from the *Arabidopsis* KCS2 coding sequence by deduction and synthesis based upon the wild-type KCS2 amino acid sequence, using the redundancy of the genetic code to formulate alternative coding sequences. Derived sequences may also be identified in different organisms, for example by isolation using as probes the nucleic acid sequences of the invention. Antibodies prepared against a KCS2 protein of the invention may also be used to identify alternative coding sequences, which are thereby derived from the coding sequence disclosed herein. Alternative KCS2 amino acid sequences of the invention, such as amino acid sequences developed through mutagenesis or substitution, may similarly be used to infer coding sequences derived from the *Arabidopsis* KCS2 coding sequence disclosed herein.

Derived nucleic acids of the invention may be obtained by chemical synthesis, isolation, or cloning from genomnic DNAs using techniques known in the art, such as the Polymerase Chain Reaction (PCR). Nucleic acids of the present invention may be used to design alternative primers (probes) suitable for use as PCR primers to amplify particular regions of an condensing enzyme cDNA of the invention. Such PCR primers may for example comprise a sequence of 15–20 consecutive nucleotides of the KCS2 CDNA of the invention. To enhance amplification specificity, primers of 20–30 nucleotides in length may also be used. Methods and conditions for PCR amplification are described in Innis et al. (1990); Sambrook et al. (1989); and Ausubel et al. (1995).

As used herein, the tern "probe" when made in reference to an oligonucleotide refers to an oligonucleotide which is capable of hybridizing to another oligonucleotide of interest. A probe may be single-stranded or double-standed. Probes are, for example, useful in the detection, identification, amplification and isolation of particular gene sequences. Oligonucleotide probes may be labelled with a "reporter molecule," so that the probe is detectable using a detection system, such as enzymatic, fluorescent, radioactive or luminescent detection systems.

Derived nucleic acids of the invention may also be identified by Southern analysis, a method by which the presence of DNA sequences in a target nucleic acid mixture are identified by hybridization to a labeled probe, comprising an oligonucleotide or DNA fragment of a nucleic acid of the invention. Probes for Southern analysis may for example be at least 15 nucleotides in length. Southern analysis typically involves electrophoretic separation of DNA digests on agarose gels, denaturation of the DNA after electrophoretic separation and transfer of the DNA to nitrocellulose, nylon, or another suitable membrane support for analysis with a radiolabeled, biotinylated, or enzyme-labeled probe as described in Sambrook et al. (1989).

In alternative embodiments, the invention includes nucleic acids that encode the plant very long chain fatty acid condensing enzyme of the invention, wherein the enzyme has an amino acid sequence that is at least 70% identical to an *Arabidopsis* KCS2 amino acid sequence disclosed herein, when optimally aligned. In alterative embodiments, the degree of identity may be between 50% and 100%, such as 60%, 80%, 90%, 95% or 99%.

As is well known in the art, some modifications and changes can be made in the structure of a polypeptide without substantially altering the biological function of that peptide, to obtain a biologically equivalent polypeptide. In one aspect of the invention, fatty acid condensing enzymes may include peptides that differ from a portion of the wild-type *Arabidopsis* KCS2 sequence by conservative amino acid substitutions. As used herein, the term "conserved amino acid substitutions" refers to the substitution of one amino acid for another at a given location in the peptide, where the substitution can be made without substantial loss of function. In making such changes, substitutions of like amino acid residues can be made, for example, on the basis of relative similarity of side-chain substituents, for example, their size, charge, hydrophilicity, hydrophilicity, and the like, and such substitutions may be assayed for their effect on the function of the peptide by routine testing.

In some embodiments, conserved amino acid substitutions may be made where an amino acid residue is substituted for another having a similar hydrophilicity value (e.g., within a value of plus or minus 2.0), where the following hydrophilicity values are assigned to amino acid residues (as detailed in U.S. Pat. No. 4,554,101, incorporated herein by reference): Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4).

In alternative embodiments, conserved amino acid substitutions may be made where an amino acid residue is substituted for another having a similar hydropathic index (e.g., within a value of plus or minus 2.0). In such embodiments, each amino acid residue may be assigned a hydropathic index on the basis of its hydrophilicity and charge characteristics, as follows: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−4.3); Pro (−1.6); His (−3.2); Glu (−3.5); Gln (−3.5); Asp (−3.5); Asn (−3.5); Lys (−3.9); and Arg (−4.5).

In alternative embodiments, conserved amino acid substitutions may be made where an amino acid residue is substituted for another in the same class, where the amino acids are divided into non-polar, acidic, basic and neutral classes, as follows: non-polar: Ala, Val, Leu, Ile, Phe, Trp, Pro, Met; acidic: Asp, Glu; basic: Lys, Arg, His; neutral: Gly, Ser, Thr, Cys, Asn, Gln, Tyr.

The nucleic acid coding sequences of the invention also include sequences that hybridize under stringent conditions to a complement of the *Arabidopsis* KCS2 coding sequence disclosed herein. The nucleic acid coding sequences of the invention may also be at least 70% identical to the *Arabidopsis* KCS2 coding sequence, when optimally aligned. Embodiments of the invention include isolated nucleic acid molecules comprising the coding sequences of the invention.

The present invention provides an isolated nucleic acid encoding a plant elongase enzyme that mediates biosynthesis of 18:0, 20:0, 22:0 and 24:0 fatty acids in plants. In a preferred embodiment, the nucleic acid encodes KCS2 identified in *Arabidopsis* shown in FIG. 1.

By isolated, it is meant that the isolated substance has been substantially separated or purified away from other biological components with which it would otherwise be associated, for example in vivo. The term 'isolated' therefore includes substances purified by standard purification methods, as well as substances prepared by recombinant expression in a host, as well as chemically synthesized substances.

The nucleic acids of this invention may be genomic or cDNA and may be isolated from cDNA or genomic libraries or directly from isolated plant DNA. Nucleic acids of this invention further include sequences corresponding to the KCS2 protein as well as sequences obtainable from the KCS2 protein or nucleic acid sequences. By corresponding is meant nucleic acid sequences, either DNA or RNA, including those which encode the KCS2 protein or a portion thereof, the promoter sequence found 5' to said encoding sequence, intron sequences not present in the cDNA, as well as sequences encoding any leader or signal peptide of a precursor protein that may not be found in the mature elongase protein. A nucleic acid of the invention may further comprise additional nucleic acids. For example, linkers, modified or unmodified restriction endonuclease sites and other nucleic acid sequences useful for cloning, expression, or purification.

Sequences having substantial identity will hybridize under stringent conditions. Hybridization to filter-bound sequences may for example, be performed in 0.5 M $NaHPO_4$, 7% sodium dodecyl sulfate (SDS), 1 mM EDTA at 65° C., and washing in 0.2×SSC/0.1% SDS at 42° C. (Ausubel et at., 1995). Alternatively hybridization to filter-bound sequences may for example, be performed in 0.5 M $NaHPO_4$, 7% sodium dodecyl sulfate (SDS), 1 mM EDTA at 65° C., and washing in 0.1×SSC/0.1% SDS at 68° C. (Ausubel et al., 1995). Hybridization conditions may be modified in accordance with known methods depending on the sequence of interest (Tijssen, 1993). Generally, stringent conditions are selected to be about 5° C. lower than the thermal melting point for the specific sequence at the defined ionic strength and pH.

A nucleic acid may also be identified by Northern analysis, a method used to identify RNAs that hybridize to a known probe such as an oligonucleotide, DNA fragment, CDNA or fragment thereof, or RNA fragment of a nucleic acid of the invention The probe is labeled with a radioisotope such as $^{32}P$, by biotinylation or with an enzyme. The RNA to be analyzed may be electrophoretically separated on an agarose or polyacrylamide gel, transferred to nitrocellulose, nylon, or other suitable membrane, and hybridized with the probe, using standard techniques well known in the art such as described in Sambrook et al. (1989)

A nucleic acid of the invention may alternatively be obtained by immunological screening. Antibodies to the KCS2 protein may be used to identify related protein in extracts of desired plant species. Two amino acid sequences are considered substantially identical if one peptide is specifically immunologically reactive with antibodies that are also specifically immunoreactive against the other peptide. Specific immunoreactivity of antibodies to peptides may be assessed using a variety of immunoassay formats, such as solid-phase ELISA immunoassays for selecting monoclonal antibodies specifically immunoreactive with a protein (Harlow and Lane, 1988).

Optimal alignment of sequences for comparisons of identity may be conducted using a variety of algorithms, such as the local homology algorithm of Smith and Waterman (1981), the homology alignment algorithm of Needleman and Wunsch (1970), the search for similarity method of Pearson and Lipman (1988), and the computerized implementations of these algorithms (such as GAP, BESTFIT, FASTA and TFASTA in the Wisconsin Genetics Software Package, Genetics Computer Group, Madison, Wis., U.S.A.). Sequence alignment may also be carried out using the BLAST algorithm described in Altschul et al. (1990), using the published default settings.

Software for performing BLAST analysis may be available through the National Center for Biotechnology Information (through the internet at http://www.ncbi.nlm.nih.gov/). The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighbourhood word score threshold. Initial neighbourhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST programs may use as defaults a word length (W) of 11, the BLOSUM62 scoring matrix (Henikoff and Henikoff, 1992*, Proc. Natl. Acad. Sci. USA* 89: 10915–10919) alignments (B) of 50, expectation (E) of 10 (which may be changed in alternative embodiments to 1 or 0.1 or 0.01 or 0.001 or 0.0001; although E values much higher than 0.1 may not identify functionally similar sequences, it is useful to examine hits with lower significance, E values between 0.1 and 10, for short regions of similarity), M=5, N=4, for nucleic acids a comparison of both stands. For protein comparisons, BLASTP may be used with defaults as follows: G=11 (cost to open a gap); E=1 (cost to extend a gap); E=10 (expectation value, at this setting, 10 hits with scores equal to or better than the defined alignment score, S, are expected to occur by chance in a database of the same size as the one being searched; the E value can be increased or decreased to alter the stringency of the search.); and W=3 (word size, default is 11 for BLASTN, 3 for other blast programs).

The BLOSUM matrix assigns a probability score for each position in an alignment that is based on the frequency with which that substitution is known to occur among consensus blocks within related proteins. The BLOSUM62 (gap existence cost=11; per residue gap cost=1; lambda ratio=0.85) substitution matrix is used by default in BLAST 2.0. A variety of other matrices may be used as alternatives to BLOSUM62, including: PAM30 (settings: 9,1,0.87); PAM70 (settings: 10,1,0.87) BLOSUMSO (settings: 10,1, 0.87); BLOSUM62 (settings: 11,1,0.82) and BLOSUM45 (settings: 14,2,0.87). One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences may be identified as sequences of the invention where the smallest sum probability in a comparison to a reference KCS2 amino acid or KCS2 nucleic acid test sequence is less than about 1, preferably less than about 0.1, more preferably less than about 0.01, and most preferably less than about 0.001.

When a position in the compared sequence is occupied by the same nucleotide or amino acid, following optimal alignment of the sequences, the molecules are considered to have identity at that position. The degree of identity between sequences is a function of the number of matching positions shared by the sequences. In terms of percentage, identity is the sum of identical positions, divided by the total length over which the sequences are aligned, multiplied by 100.

It will be recognized by one of ordinary skill in the art that nucleic acids of this invention may be modified using standard techniques of site specific mutation or PCR, or modification of the sequence may be accomplished in producing a synthetic nucleic acid sequence. Such modified sequences are also considered in this invention. For example, due to the degeneracy of the genetic code, which is well-known to the art; i.e., for many amino acids, there is more than one nucleotide triplet which serve as the codon for the amino acid, codons may be changed such that the nucleic acid sequence encodes the same amino acid sequence, or alternatively, codons may be altered such that conservative amino acid substitutions or substitutions of similar amino acids result without affecting protein function.

In another aspect of the invention, the nucleic acid may further comprise a promoter operably linked to the enzyme-encoding region. A first nucleic acid sequence is operably linked with a second nucleic acid sequence when the first nucleic acid sequence is placed in a fuctional relationship with the second nucleic acid sequence. For instance, a promoter is operably linked to a coding sequence if the promoter affects the transcription or expression of the coding sequences. Generally, operably linked DNA sequences are contiguous and, where necessary to join two protein coding regions, in reading flame.

A promoter, as used herein, is a DNA sequence in a gene, usually (but not necessarily) upstream (5') to its coding sequence, which controls the expression of the coding sequence by providing the recognition for RNA polymerase and other factors required for proper transcription. In artificial DNA constructs promoters may also be used to transcribe antisense RNA. Promoters may also contain DNA sequences that are involved in the binding of protein factors which control the effectiveness of transcription initiation in response to physiological or developmental conditions. A promoter may also contain enhancer elements, a DNA sequence which can stimulate promoter activity. A gene of the present invention may also include transcription termination signals.

In one embodiment of the invention, the nucleic acid may be used to alter the composition and accumulation of fatty acids in plant cells. For example, for over-expression, which refers to production of a gene product exceeding levels of production in normal or non-transformed organisms, a plant promoter may be employed which will direct expression of the elongase in all tissues of a regenerated plant. Over-expression of the gene, for example, in plant epidermal cells could increase cuticle accumulation thereby increasing drought and stress tolerance of transgenic plants over control plants. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens*, and other transcription initiation regions from various plant genes known to those of skill in the art.

In various embodiments, the invention comprises plants transformed with the nucleic acids of the invention. In some embodiments, such plants will exhibit altered fatty acid content in one or more tissues. These aspects of the invention relate to all higher plants, including monocots and dicots, such as species from the genera *Fragaria, Lotus, Medicago, Onobrychis, Triforium, Trigonelia, Wgna, Citrus, Linum, Geranium, Manihot, Caucus, Arabidopsis, Brassica, Raphanus, Sinapis, Atropa, Capsicum, Hyoscyamus, Lycopersicon, Nicotiana, Solanum, Petunia, Digitalis, Majorana, Cichorium, Helianthus, Lactuca, Bromus, Asparagus, Antirrhinum, Heterocatlis, Nemesia, Pelargonium, Panicum, Penniserum, Ranunculus, Senecio, Salpiglossis, Cucarnis, Browallia, Glycine, Lolium, Zea, Triticurm Sorghum*, and *Datura*. Such plants may include maize, wheat, rice, barley, soybean, beans, rapeseed, canola, alfalfa, flax, sunflower, cotton, clover, lettuce, tomato cucurbits, potato canot, radish, pea lentils, cabbage, broccoli, brussel sprouts, peppers, apple, pear, peach, apricot, carnations and roses. More specifically, in alternative embodiments, plants for which the invention may be used in modifying fatty acid content include oil crops of the Cruciferae family: canola, rapeseed (*Brassica* spp.), crambe (*Crambe* spp.), honesty (*Lunaria* spp.) lesquerella (*Lesquerela* spp.), and others; the compositae family: sunflower (*Helianthus* spp.), safflower (*Carthamus* spp.), niger (*Guizotia* spp.) and others; the Palmae family: palm (*Elaeis* spp.), coconut (*Cocos* spp.) and others; the Leguminosae family: peanut (*Arachis* spp.), soybean (*Glycine* spp.) and others; and plants of other families such as maize (*Zea* spp.), cotton (*Gossvpiun* sp.), jojoba (*Simonasia* sp.), flax (*Linum* sp.), sesame (*Sesamum* spp.), castor bean (*Ricinus* spp.), olive (*Olea* spp.), poppy (*Papaver* spp.), spurge (*Euphorbia,* spp.), meadowfoam (*Limnanthes* spp.), mustard (*Sinapis* spp.) and cuphea (*Cuphea* spp.).

The promoter of the invention may direct expression of the elongase gene in a specific tissue or may be otherwise under more precise environmental or developmental control. Such promoters are referred to here as "inducible" promoters. Examples of environmental conditions that may effect transcription by inducible promoters include anaerobic conditions, elevated temperature, or the presence of light. Examples of promoters under developmental control include promoters that initiate transcription only in certain tissues, such as fruit, seeds, or flowers.

In other embodiments, a nucleic acid disclosed herein may be used for cosuppression or antisense inhibition. Antisense inhibition refers to the production of antisense RNA transcripts capable of preventing or reducing the expression of the target protein. The term "antisense" as used herein refers to a nucleotide sequence in which the sequence of residues is in reverse 5' to 3' orientation in relation to the sequence of residues in a sense strand of a nucleic acid coding sequence. A "sense" or "coding" strand or sequence refers to a sequence that may be transcribed by a cell into an mRNA encoding a protein. An "antisense" sequence will therefore generally have the same sequence as the noncoding strand in a DNA duplex, and an antisense RNA will be complementary to an "antisense" sequence. Co-supression refers to the phenomenon in which expression of a foreign gene which has substantial homology to an endogenous gene results in the suppression of expression of both the foreign and the endogenous gene.

As used herein, the terms "complementary" or "complementarity" when used in reference to polynucleotides refer to polynucleotides which are related by the base-pairing rules, including the rules governing complementarity between DNA and RNA. For example, the sequence 5'-AGT-3' is complementary to the sequence 5'-ACT-3'.

In another embodiment of the invention, the KCS2 promoter disclosed herein may be operably linked to agronomically important genes, other than the elongase gene disclosed in the present invention. For example, the KCS2 promoter may be operably linked to the Bt gene, encoding a protein insecticide, to confer insect resistance on the transformed plant (U.S. Pat. No. 5,723,756). The KCS2 promoter may be operably linked to genes encoding proteins, which have fungal, bacterial and viral inhibiting effects, such as lysozyme, chitinase, attacin, and cecropin (U.S. Pat. No. 5,597,946) to confer fungal/bacterial resistance on transformed plants.

A cell, tissue, organ, or organism into which has been introduced a foreign nucleic acid, is considered "transformed", "transfected", or "transgenic". A transgenic or transformed cell or organism also includes progeny of the cell or organism and progeny produced from a breeding program employing a transgenic plant as a parent in a cross and exhibiting an altered phenotype resulting from the presence of a recombinant nucleic acid construct. A transgenic plant is therefore a plant that has been transformed with a heterologous nucleic acid, or the progeny of such a plant that includes the transgene. The invention provides vectors, such as vectors for transforming plants or plant cells. The term "vector" in reference to nucleic acid molecule generally refers to a molecule that may be used to transfer a nucleic acid segment(s) from one cell to another.

Another aspect of the invention provides transgenic plant cells, plant tissues derived from such plant cells, and descendants thereof. Nucleic acids of the invention may be introduced into the genome of the desired plant host by a variety of conventional techniques which include, without limitation, electroporation and microinjection of plant cell prototplasts and polyethylene glycol precipitation (such as are disclosed in Paszkowski et al, (1984); Fromm et al., (1985); Rogers et al., (1986); and in U.S. Pat. Nos. 4,684,611; 4,801,540; 4,743,548 and 5,231,019), ballistic methods such as DNA particle bombardment (for example as disclosed in Klein, et al. (1987); Gordon-Kamm, et al. (1990); and in U.S. Pat. Nos. 4,945,050; 5,015,580; 5,149,655 and 5,466,587); *Agrobacterium*-mediated transformation methods (such as those disclosed in Horsch et al. *Science* (1984); Fraley et al., (1983); and U.S. Pat. Nos. 4,940,838 and 5,464,763). Alternative transfonnation protocols are disclosed for example in U.S. Pat. No. 5,584,807; 5,501,967; Fraley et al. (1982) *Proc. Natl. Acad. Sci. USA* 79:1859–1863; Krens et al. (1982) *Nature* 296:72–74).

Transformed plant cells, which may be derived by any of the above transforation techniques, may be cultured to regenerate whole plants having the transformed genotype and displaying a desired phenotype, as for altered VLCFA levels. A variety of plant culture techniques may be used to regenerate whole plants, such as described in Gamborg and Phillips (1995); Evans et al. (1983); or Binding, (1985); or in Klee (1987).

One of skill will recognize that after the nucleic acid is stably incorporated in transgenic plants and corned to be operable, it can be introduced into other plants by sexual crossing. Any of a number of standard breeding techniques may be used depending upon the species to be crossed.

Nucleic acids of the invention may also be used as a plant breeding tool, as molecular markers to aid in plant breeding programs. Such techniques would include using the gene itself as a molecular probe or using the DNA sequence to design PCR primers to use PCR based screening techniques in plant breeding programs.

The invention now being generally described, it will be more readily understood by references to the following examples, which are included for purposes of illustration only and are not intended to limit the invention unless so stated.

EXAMPLE 1

Cloning KCS2

Following discovery and sequencing of the region of KCS2 in *Arabidopsis*, synthetic oligonucleotides homologous to portions of the KCS2 genornic sequence were prepared and used as primers to amplify either 1508 bp or 1001 bp of continuous KCS2 DNA sequence by PCR. As shown in FIG. 1, the upstream primer was 5'-GTATCATCAACAAAAATATC-3' (kcs1) in combination with the downstream primer 5'-CAAAGATCGATCTTAACC-3' (kcs2) for the PCR-synthesis of the 1508 bp genomic DNA fragment, which includes a complete coding sequence. Primers 5'-CGATCACGGAGTAGAGAA-3' (kcs3) and 5'-GGACAGTTCTAAAGCAG-3' (kcs4) were used for the PCR-amplification of the 1001 bp of the 5' untranslated region (promoter fragment). The amplified 1508 bp fragment was subcloned in the EcoRI site of the plasmid pCR2.1 (Invitrogen) to produce plasmid pCR-KCS2, whereas the 1001 bp promoter fragment was subcloned in the SmaI site of the plasmid pGEM7zf(Promega) to produce plasmid pGEM-proKCS2. The cloned DNA fragments were then completely sequenced on both strands using an automatic sequencer by the dideoxy chain termination method. These two fragments together comprise 2508 bp of continuous genomic DNA sequence shown in FIG. 1. This DNA sequence represents a 1001 bp 5' untranslated region (i.e., nucleotides preceding the first ATG codon), and a 1461 bp open reading frame that encodes a 487 amino acid protein with a predicted molecular weight of 54,900 Da (KCS2).

EXAMPLE 2

Expression of KCS2 in Yeast

The full length KCS2 cDNA was expressed in *Saccharomyces cerevisiae* linked to the GAL10 inducible promoter. The KCS2 gene was cleaved from pCR2.1 with EcoRI and inserted into the EcoRI site of the polylinker of the *S. cerevisiae* expression vector pESC-TRP (Stratagene), resulting in the plasmid pESC-KCS2. The construct was transformed into the *S. cerevisiae* strain YPHY99 by standard procedures (Schiestl and Gietz, 1989) and transformants selected on minimal medium agar plates lacking tryptophan (Ausubel et al., 1995).

When yeast cells harboring the pESC-KCS2 construct were grown in the presence of galactose, 18:0, 20:0, 22:0 and 24:0 fatty acids accumulated (which are not normally present in the YPHY99 yeast stain, and were not detected in cultures of yeast transformed with the pESC plasmid alone). Previous work on FAE1 indicates that the yeast expression system is a predictive model of elongase condensing enzyme activity in plants (Millar and Kunst, 1997). Accordingly, the yeast expression results disclosed herein shows that the KCS2 gene encodes an elongase (condensing) enzyme capable of mediating biosynthesis of saturated VLCFAs, including 18:0, 20:0, 22:0 and 24:0 fatty acids, in a wide variety of organisms.

EXAMPLE 3

Activity of the Tissue-Specific KCS2 Promoter

In order to confirm and more precisely delineate KCS2 expression patterns, 5' flanking sequences from the KCS2 genomic clone were transitionally fused (operatively linked) to the uidA reporter gene encoding beta-glucuronidase (GUS). The inserts were cleaved out of pGEM7zf with BamHI and XbaI and directionally subcloned into the corresponding sites of the binary Ti plasmid pBI101 (Clontech), which contains a promoterless GUS gene (Jefferson et al. 1987). The pKCS2-GUS fusion construct in pBI101 was introduced into *Agrobacterium tumefaciens* strain GV3101 (Koncz and Schell, 1986) by heat-shock and selected for resistance to kanamycin (50 (g/ml).

The pKCS2-GUS fusion was introduced into *Arabidopsis* using the floral dip method (Clough and Bent, 1998). Screening for transformed seed was done on 50 micrograms/mL kanamycin as described previously (Katavic et al., 1994). The KCS2 promoter expression pattern was determined using GUS histochemical assays using buffer containing X-GLUC on whole seedlings, leaves at different sages of development, stems, flowers, siliques and roots on a large number of pKCS2-GUS transgenic lines. Wild type plants treated with GUS buffer under the same conditions were used as controls.

The expression pattern observed for the KCS2 promoter in the pKCS2-GUS fusion was consistent in all transgenic lines tested. GUS activity was only observed in the anthers and very young emerging leaves (1–2 mm in size). No GUS expression was detected in any of the other tissues or the wild type controls. Expression of KCS2 in the anthers was confirmed by RNA blot analysis, using the full KCS2 ORF (Open Reading Frame) as a probe, confirming that the *Arabidopsis* KCS2 promoter mediates the expression of heterologous proteins in a tissue specific manner.

EXAMPLE 4

Analysis of the Specificity of the KCS2 Gene Product

Expression of the KCS2 gene under the control of GAL10, a galactose-inducible promoter in yeast cells expressing pESC-KCS2 results in the appearance of four extra peaks in GC chromatograms. These peaks correspond to the saturated VLCFAs 20:0, 22:0, 24:0 and 26:0, suggesting KCS2 condensing enzyme can elongate fatty acids from C18 to C24 in length.

To test the ability of KCS2 to elongate an acyl chain in planta, the full KCS2 coding sequence was placed behind the FAE1 seed specific promoter. The recipient plant used for the experiment was the mutant CB25, which contains a lesion in the FAE1 gene, resulting in a truncated FAE1 protein. Thus, CB25 plants do not make VLCFAs in the seeds, and all the VLCFAs observed would be the product of the KCS2 condensing enzyme.

Gas chromatography analysis was performed on seeds of 50 transgenic lines and compared to CB25 seeds. A number of lines showed a fatty acid profile different from the one observed for CB25 seeds. The most dramatic difference was observed in the levels of mono-unsaturated C20:1 fatty acid, which in some lines shows an increase of almost 100-fold when compared to the control, followed by C22:1 fatty acid and C20:0 fatty acid, as shown in Table 1.

TABLE I

Fatty Acid Profile of KCS2 Expression

| FA | CB25 % area | 5–6 % area | 5–15 % area | 5–8 % area | 6–8 % area | 5–10 % area | 5–16 % area | 6–7 % area |
|---|---|---|---|---|---|---|---|---|
| 16:0 | 12.18 | 8.93 | 9.58 | 8.89 | 11.70 | 8.65 | 9.22 | 9.44 |
| 16:1 | 0.67 | 0.41 | 0.53 | 0.46 | 0.77 | 0.39 | 0.43 | 0.61 |
| 18:0 | 2.92 | 3.69 | 4.85 | 3.93 | 2.92 | 3.01 | 3.49 | 3.49 |
| 18:1 | 27.59 | 20.86 | 19.95 | 14.07 | 15.16 | 20.09 | 25.37 | 12.52 |
| 18:2 | 33.47 | 29.90 | 28.98 | 27.62 | 28.83 | 30.72 | 30.97 | 29.06 |
| 18:3 | 22.02 | 23.12 | 19.15 | 21.60 | 22.12 | 22.18 | 23.32 | 20.67 |

TABLE I-continued

Fatty Acid Profile of KCS2 Expression

| FA | CB25 % area | 5–6 % area | 5–15 % area | 5–8 % area | 6–8 % area | 5–10 % area | 5–16 % area | 6–7 % area |
|---|---|---|---|---|---|---|---|---|
| 20:0 | 0.63 | 1.13 | 1.84 | 2.10 | 1.35 | 1.11 | 0.87 | 1.82 |
| 20:1 | 0.24 | 11.16 | 14.02 | 19.49 | 15.73 | 12.89 | 5.74 | 20.45 |
| 22:0 | 0.16 | 0.19 | 0.25 | 0.29 | 0.23 | 0.19 | 0.18 | 0.25 |
| 22:1 | 0.00 | 0.45 | 0.66 | 1.32 | 0.10 | 0.63 | 0.26 | 1.55 |
| 24:1 | 0.10 | 0.14 | 0.17 | 0.21 | 0.17 | 0.14 | 0.14 | 0.14 |

The identity of the peaks was estimated by comparing their retention times to known fatty acid standards.

EXAMPLE 5

Utility of KCS2 for Seed Oil Modification

Results of the experiments described above show that the KCS2 gene is primarily expressed in flower buds and demonstrate that KCS2 condensing enzyme can elongate VLCFAs in *Arabidopsis* seeds. In an attempt to co-suppress KCS2 in order to obtain a loss-of-function phenotype, as well as a gain-of-function, over-expression phenotype, the strong CaMV 35S promoter was used to constitutively express KCS2 in all plant tissues.

RNA blot analyses carried out on randomly selected transgenic lines to assess the level of expression of the 35S-KCS2 transgene demonstrated high levels of expression of the KCS2 gene in a number of lines. To determine whether high levels of the KCS2 expression translated into higher levels of VLCFAs in the seed, seed of the 35S-KCS2 plants showing the highest levels of the KCS2 transcript were subjected to gas chromatography analyses.

Fatty acid profiles of all the transgenic lines tested differ significantly from the wild type as shown in FIG. 2. The main difference was observed in the level of 20:1 fatty acid (approximately 18% versus 12% in wild type), and a retied 18:1 content. Apparently, the expression of KCS2 in seeds increases the rate of conversion of 18:1 to 20:1 fatty acids and as a result, all the transgenic 35S-KCS2 lines accumulate significantly more total VLCFAs than the wild type seeds. A calculation of the proportion of VLCFAs with respect to total fatty acids showed that all the transgenic lines tested have over 20% of VLCFAs, whereas in the wild type VLCFAs account for 16.9% of total fatty acids.

REFERENCES

All publications, including patent applications referred to herein and including the following, are hereby incorporated by reference:

WO 95/15387
WO 96/13582
U.S. Pat. No. 4,940,838
U.S. Pat. No. 5,464,763
U.S. Pat. No. 4,945,050
U.S. Pat. No. 5,015,580
U.S. Pat. No. 5,149,655
U.S. Pat. No. 5,466,587
U.S. Pat. No. 4,684,611
U.S. Pat. No. 4,801,540
U.S. Pat. No. 4,743,548
U.S. Pat. No. 5,231,019
U.S. Pat. No. 5,597,946
U.S. Pat. No. 5,723,756

Ausubel, F. M. et al. eds., (1995) Current Protocols in Molecular Biology (New York: John Wiley and Sons).

Altschul S. F. et al. (1990) Basic local alignment search tool. J Mol Biol. 215(3):403–410.

Binding, "Regeneration of Plants, Plant Protoplasts", CRC Press, Boca Raton, 1985.

Clough, S. J. and Bent, A. F. (1998) Floral dip: a simplified method for *Agrobacterium*-mediated transformation of *Arabidopsis thaliana*. Plant J. 16: 735–743.

Evans et al. "Protoplasts Isolation and Culture". Handbook of Plant Cell Culture, Macmillan Publishing Company, New York, 1983.

Fraley et al., Proc. Natl. Acad. Sci. USA 80:4803 (1983).

Fromm et al., Proc. Natl. Acad. Sci. USA 82:5824 (1985).

Gamborg and Phillips, "Plant Cell, Tissue and Organ Culture, Fundamental Methods", Springer Berlin, 1995.

Gordon-Kamm, et al. "The Plant Cell" 2:603 (1990).

Haque, M. M. et al.(1992) Inheritance of leaf epicuticular wax content in rice. Crop Sci. 32: 865–868.

Harlow and Lane (1988) *Antibodies. A Laboratory Manual*, Cold Spring Harbor Publicarions, New York.

Horsch et al. *Science* 233:496 (1984).

Innis, et al. eds. PCR Protocols. A Guide to Methods and Application. (Academic Press, Inc. San Diego, Calif. 1990).

James, D. W. and Dooner, H. K. (1990) Isolation of EMS induced mutations in *Arabidopsis* altered in seed fatty acid composition. Theoretical and Applied Genetics 80: 241–245.

Jefferson. R. A. et al. (1987) GUS fusions: -glucuronidase as a sensitive and versatile gene fusion marker system in higher plants. *EMBO J*. 6: 3901–3907.

Katavic. V. et al. (1994) In plant transformation of *Arabidopsis thaliana*. Mol.Gen.Genet. 245: 363–370.

Klee er al., *Ann. Rev. of Plant Phys*. 38:467 (1987).

Klein, et al., *Nature* 327:70 (1987).

Koncz, C. and Schell, J. (1986) The promoter of TL-DNA gene 5 controls the tissue-specific expression of chimeric genes carried by a novel type of *Agrobacterium* binary vector. *Mol. Gen. Genet*. 204: 383–396.

Kunst, L. et al. (1992) Fatty Acid Elongation in developing seeds of *Arabidopsis thaliana*. Plant Physiol. Biochem. 30: 425–434.

Lassner et al. (1996) A Jojoba β-keto-acyl-coA-synthase cDNA compliments the Canola fatty acid elongation mutation in trazigenic plants. Plant Cell 8: 281–292.

Lemieux et al. (1990) Mutants of *Arabidopsis* with alterations in seed lipid fatty acids. Theoretical and Applied Genetics 80: 234–240.

Millar. A. A., and Kunst, L. (1997) Very-long-chain fatty acid biosynthesis is controlled through the expression and specificity of the condensing enzyme. Plant J. 12: 121–131.

Millar, A. A. et al. (1999) CUT1, an *Arabidopsis* gene required for cuticular wax biosynthesis and pollen fertility, encodes a very-long-chain fatty acid condensing enzyme. Plant Cell 11: 825–838.

Needleman and Wunsch (1970) J. Mol. Biol. 48:443.

O'Toole, J. C. and Cruz, R. T. (1983) Genotypic variation in epicuticular wax of rice. Crop Sci. 23: 392–394.

Paszkowski et al. *EMBO J*. 3:2717 (1984).

Pearson and Lipman, 1988*, Proc. Natl. Acam. Sci. USA* 85:2444.

Post-Beittenmiller, D. (1996) Biochemistry and molecular biology of wax production in plants. *Annu. Rev. Plant Physiol. Mol. Biol*. 47: 405–430.

Rogers el al., *Methods Enzymol*. 118:627 (1986).

Sambrook, et al. Molecular Cloning: A Laboratory Manual. ($2^{nd}$ ed., Vols. 1–3, Cold Spring Harbor Laboratory (1989).

Schiestl, R. H., and Gietz, R. D. (1989) High efficiency transformation of intact yeast cells using single standed nucleic acids as a carrier. Curr. Genet. 16: 339–346.

Smith and Waterman (1981) Adv. Appl. Math 2:482.

Tijssen, (1993) Laboratory Techniques in Biochemistry and Molecular Biology-Hybridization with Nucleic Acid Probes, Part I, Chapter 2 "Overview of Principles in Hybridization and the Strategy of Nucleic Acid Probe Assavs" (Elsevier, N.Y.).

CONCLUSION

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the specification, the word "comprising" is used as an open-ended term, substantially equivalent to the phrase "including, but not limited to", and the word "comprises" has a corresponding meazing. Citation of references herein shall not be construed as an admission that such references are prior art to the present invention. All publications, including but not limited to patents and patent applications, cited in this specification are incorporated herein by reference as if each individual publication were specifically and individually indicated to be incorporated by reference herein and as though fully set forth herein.

What is claimed is:

1. A recombinant nucleic acid molecule comprising a heterologous polynucleotide selected from the group consisting of:

(a) a nucleic acid coding sequence having at least 95% sequence identity to the *Arabidopsis* KCS2 coding sequence shown at position 1046–2509 of SEQ ID NO: 1, when optimally aligned, wherein the sequence encodes a plant very long chain fatty acid condensing enzyme that catalyses condensation of malonyl-CoA with a C16, C18, C20, or C22 acyl-CoA; and (b) a complementary nucleic acid sequence fully complementary to the nucleic acid sequence of (a).

2. The recombinant nucleic acid molecule of claim 1 wherein the nucleic acid coding sequence is the *Arabidopsis* KCS2 coding sequence shown at position 1046–2509 of SEQ ID NO: 1.

3. The recombinant nucleic acid molecule of claim 1 wherein the nucleic acid coding sequence hybridizes under stringent conditions to the complement of the *Arabidopsis* KCS2 coding sequence shown at position 1046–2509 of SEQ ID NO: 1.

4. A transgenic plant comprising the recombinant nucleic acid molecule of claim 1.

5. A part of a transgenic plant comprising the recombinant nucleic acid molecule of claim 1.

6. The transgenic plant of claim 4, wherein the transgenic plant has a modified phenotype compared to a non-transgenic plant of the same species.

7. The transgenic plant of claim 4, wherein the plant is a monocot.

8. The transgenic plant of claim 4, wherein the plant is a dicot.

9. The transgenic plant of claim 4, wherein the plant is a species of one of the Cruciferae family, Compositae family, Palmae family, or Leguminosae family.

10. The transgenic plant of claim 4, wherein the plant is selected from the group consisting of: canola, rapeseed (*Brassica* spp.), crambe (*Crambe* spp.), honesty (*Lunaria* spp.) lesquerella (*Lesquerela* spp.), sunflower (*Helianthus* spp.), safflower (*Carthamus* spp.), niger (*Guizotia* spp.), palm (*Elaeis* spp.), coconut (*Cocos* spp.), peanut (*arachis* spp.), soybean (*Glycine* spp.), (*Zea* spp.), cotton (*Gossypium* sp.), jojoba (*Simmondsia* sp.), flax (*Linum* sp.), sesame (*Sesamum* spp.), castor bean (*Ricinus* spp.), olive (*Olea* spp.), poppy (*Papaver* spp.), spurge (*Euphorbia* spp.), meadowfoam (*Limnanthes* spp.), mustard (*Sinapis* spp.) and cuphea (*Cuphea* spp.).

11. A transgenic seed comprising the recombinant nucleic acid molecule of claim 1.

12. The transgenic seed of claim 11, wherein the seed is for a plant of the species of one of the Cruciferae family, Compositae family, Palmae family, or Leguminosae family.

13. The transgenic seed of claim 11, wherein the seed is for a plant selected from the group consisting of: canola, rapeseed (*Brassica* spp.), crambe (*Crambe* spp.), honesty (*Lunaria* spp.) lesquerella (*Lesquerela* spp.), sunflower (*Helianthus* spp.), safflower (*Carthamus* spp.), niger (*Guizotia* spp.), palm (*Elaeis* spp.), coconut (*Cocos* spp.), peanut (*arachis* spp.), soybean (*Glycine* spp.), (*Zea* spp.), cotton (*Gossypium* sp.), jojoba (*Simmondsia* sp.), flax (*Linum* sp.), sesame (*Sesamum* spp.), castor bean (*Ricinus* spp.), olive (*Olea* spp.), poppy (*Papaver* spp.), spurge (*Euphorbia* spp.), meadowfoam (*Limnanthes* spp.), mustard (*Sinapis* spp.) and cuphea (*Cuphea* spp.).

14. A transgenic cell comprising the recombinant nucleic acid of claim 1.

15. The transgenic cell of claim 14, wherein the cell is a non-human cell.

16. The transgenic cell of claim 14, wherein the cell is a plant cell.

17. A recombinant expression vector comprising the recombinant nucleic acid molecule of claim 1.

18. A recombinant expression cassette comprising the recombinant nucleic acid molecule of claim 1 operably linked to a promoter.

19. An isolated nucleic acid molecule comprising a polynucleotide selected from the group consisting of:

(a) a nucleic acid coding sequence having at least 95% sequence identity to the *Arabidopsis* KCS2 coding sequence shown at position 1046–2509 of SEQ ID NO: 1, when optimally aligned, wherein the sequence encodes a plant very long chain fatty acid condensing enzyme that catalyses condensation of malonyl-CoA with a C16, C18, C20, or C22 acyl-CoA; and (b) a complementary nucleic acid sequence fully complementary to the nucleic acid sequence of (a).

20. The isolated nucleic acid molecule of claim 19 wherein the nucleic acid coding sequence is the *Arabidopsis* KCS2 coding sequence shown at position 1046–2509 of SEQ ID NO: 1.

21. The isolated nucleic acid molecule of claim 19 wherein the nucleic acid coding sequence hybridizes under stringent conditions to the complement of the *Arabidopsis* KCS2 coding sequence shown at position 1046–2509 of SEQ ID NO: 1.

22. A method of producing a transgenic plant, the method comprising introducing into the plant the isolated nucleic acid molecule of claim 19.

23. A progeny plant produced by sexual or asexual propagation of the transgenic plant produced by the method of claim 22 or produced by propagation of the progeny plant, wherein the progeny plant comprises the nucleic acid molecule.

24. A transgenic plant comprising the isolated nucleic acid molecule of claim 19.

25. A part of a transgenic plant comprising the isolated nucleic acid molecule of claim 19.

26. The transgenic plant of claim 24, wherein the transgenic plant has a modified phenotype compared to a non-transgenic plant of the same species.

27. The transgenic plant of claim 26, wherein the plant is a monocot.

28. The transgenic plant of claim 26, wherein the plant is a dicot.

29. The transgenic plant of claim 26, wherein the plant is a species of one of the Cruciferae family, Compositae family, Palmae family, or Leguminosae family.

30. The transgenic plant of claim 26, wherein the plant is selected from the group consisting of: canola, rapeseed (*Brassica* spp.), crambe (*Crambe* spp.), honesty (*Lunaria* spp.) lesquerella (*Lesquerela* spp.), sunflower (*Helianthus* spp.), safflower (*Carthamus* spp.), niger (*Guizotia* spp.), palm (*Elaeis* spp.), coconut (*Cocos* spp.), peanut (*arachis* spp.), soybean (*Glycine* spp.), (*Zea* spp.), cotton (*Gossypium* sp.), jojoba (*Simmondsia* sp.), flax (*Linum* sp.), sesame (*Sesamum* spp.), castor bean (*Ricinus* spp.), olive (*Olea* spp.), poppy (*Papaver* spp.), spurge (*Euphorbia* spp.), meadowfoam (*Limnanthes* spp.), mustard (*Sinapis* spp.) and cuphea (*Cuphea* spp.).

31. A transgenic seed comprising the isolated nucleic acid molecule of claim 19.

32. The transgenic seed of claim 31, wherein the seed is for a plant of a species of one of the Cruciferae family, Compositae family, Palmae family, or Leguminosae family.

33. The transgenic seed of claim 31, wherein the seed is for a plant selected from the group consisting of: canola, rapeseed (*Brassica* spp.), crambe (*Crambe* spp.), honesty (*Lunaria* spp.) lesquerella (*Lesquerela* spp.), sunflower (*Helianthus* spp.), safflower (*Carthamus* spp.), niger (*Guizotia* spp.), palm (*Elaeis* spp.), coconut (*Cocos* spp.), peanut (*arachis* spp.), soybean (*Glycine* spp.), (*Zea* spp.), cotton (*Gossypium* sp.), jojoba (*Simmondsia* sp.), flax (*Linum* sp.), sesame (*Sesamum* spp.), castor bean (*Ricinus* spp.), olive (*Olea* spp.), poppy (*Papaver* spp.), spurge (*Euphorbia* spp.), meadowfoam (*Limnanthes* spp.), mustard (*Sinapis* spp.) and cuphea (*Cuphea* spp.).

34. A transgenic cell comprising the isolated nucleic acid molecule of claim 19.

35. The transgenic cell of claim 34, wherein the cell in non-human cell.

36. The transgenic cell of claim 34, wherein the cell is a plant cell.

37. A recombinant expression vector comprising the isolated nucleic acid molecule of claim 19.

38. A recombinant expression cassette comprising the isolated nucleic acid molecule of claim 19 operably linked to a promoter.

* * * * *

SEQUENCE LISTING

```
<160> NUMBER OF SEQ ID NOS: 5

<210> SEQ ID NO 1
<211> LENGTH: 2509
<212> TYPE: DNA
<213> ORGANISM: Arabidopsis sp.

<400> SEQUENCE: 1

tgttgtggag gacttgtgag aaccaccacc agagtccgac atcgcgatca cggagtagag     60
```

-continued

```
aaagtcaaaa ctacttctct cagacggatt agtttggttt gctggagatt gttccaagaa    120
agagaaacgt taggagcaaa caaacaaaag agaaaagacg atgatgactg atgagagctt    180
taacaaaaaa ataaaatgag agagctcaac gggtagaatt gtgagacttg agagagtgtt    240
tcctatttaa ggcatgcgat tagtgtttat tacgagaatg ccaccgaacg agtacatatt    300
aatgtatagt atgttaatga tagtctaact aaaatttggt ttttattgaa atagaatttt    360
gtaagaataa tgaggatctg taatatagct ggatttgcat taaatcgtac gccgttggta    420
atcgaaatta gttaaataaa tgttttagca tataatgttg gtgcttccga catgtttatt    480
ggacaataat accatatttt ttctttggga tcttaaaaaa attgaggaag aaaatagtaa    540
aatagtcaaa cttaggttac atcataatgg gccaattctt tgagttgtga ttgatctcca    600
aagatataca tagatttaca caagatcaaa agaaaaacaa ttgggcctaa accccaagcc    660
catatcaacg tccattatca ttaagattcc ttttttctt gaaatttgaa aatttgaaat    720
tcgattcaaa tctactctct ctgttttttt cccataaaaa tctgaaaaac cagaagcttc    780
ttcatcactt ttcctcttga tatcttccat tagttggccg atacacatga cgccaaatac    840
atcaatggcg actcttctct gtttttagt tatatcaaac tcccacccaa cctgcagaag    900
aaaaaatggt gtctataaac acatcccctt acgatttctt ctctatctct ctcacagtat    960
ctatatatac gcacacaaac ccagattcag tttctcatca gtatcatcaa caaaaatatc   1020
aaagattctg ctttagaaac tgtccatgga tgctaatgga ggacctgtac agatccggac   1080
ccaaaactac gtcaagcttg gttatcacta tctgatcact cactttttta aactcatgtt   1140
cctccctcta atggctgttt tgttcatgaa tgtctcattg ttaagcctaa accatcttca   1200
gctctattac aattccaccg gattcatctt cgtcattact ctcgccattg tcggatccat   1260
tgtcttcttc atgtctcgac ctagatccat ctaccttcta gattactctt gctacctccc   1320
gccttcgagt caaaaagtta gctaccagaa attcatgaac aactctagtt tgattcaaga   1380
tttcagcgaa acttctcttg agttccagag gaagatcttg attcgctctg gtctcggtga   1440
agagacttat ttaccggatt ctattcactc tatccctccg cgtcctacta tggctgcagc   1500
gcgtgaagaa gcggagcagg taatcttcgg tgcactcgac aatcttttcg agaatacaaa   1560
aatcaatcct agggagattg gtgttcttgt tgtgaattgt agtttgttta accctacgcc   1620
ttctttatcc gccatgattg ttaacaagta taagcttaga ggaaacatta agagctttaa   1680
ccttggagga atgggatgta gtgctggtgt tatcgcggta gatctagcta gtgatatgtt   1740
acaaatccat aggaacactt ttgctcttgt ggttagtact gagaacatca ctcagaattg   1800
gtattttggt aacaagaaag caatgttgat ccctaattgc ttgtttagag ttggtggttc   1860
cgcggttctg ctttcgaaca agcctttgga tcgaaaacga tccaagtata agcttgttca   1920
tacggtcagg actcataaag gatctgatga gaacgcattc aattgtgtgt atcaagaaca   1980
agatgagtgt ttgaaaaccg gagtttcttt gtctaaagat cttatggcta tagctggaga   2040
agctttaaag acgaatatca cttctttggg tcctctggtt cttcctataa gcgagcagat   2100
tctgttcttt gcgacttttg ttgctaagag attgttcaat gacaagaaga agaagcctta   2160
cataccggat ttcaagcttg ctttagatca tttctgtatt cacgcgggag gtagagccgt   2220
gattgatgag ctagagaaga gtttaaagct ttctccaaaa catgttgagg cgtctagaat   2280
gactttgcat agatttggaa acacttcctc tagctctata tggtatgaat tggcttacac   2340
ggaagctaaa ggaagaatga ggaaaggaaa cagagtttgg cagattgctt ttggtagcgg   2400
gtttaagtgt aacagcgcgg tttgggtggc tcttcgcaat gtcgagccct cggttaacaa   2460
```

-continued

```
tccttgggaa cattgcatcc atagatatcc ggttaagatc gatctttga          2509


<210> SEQ ID NO 2
<211> LENGTH: 20
<212> TYPE: DNA
<213> ORGANISM: Arabidopsis sp.

<400> SEQUENCE: 2

gtatcatcaa caaaaatatc                                           20


<210> SEQ ID NO 3
<211> LENGTH: 18
<212> TYPE: DNA
<213> ORGANISM: Arabidopsis sp.

<400> SEQUENCE: 3

caaagatcga tcttaacc                                             18


<210> SEQ ID NO 4
<211> LENGTH: 18
<212> TYPE: DNA
<213> ORGANISM: Arabidopsis sp.

<400> SEQUENCE: 4

cgatcacgga gtagagaa                                             18


<210> SEQ ID NO 5
<211> LENGTH: 18
<212> TYPE: DNA
<213> ORGANISM: Arabidopsis sp.

<400> SEQUENCE: 5

ggacagtttc taaagcag                                             18
```